US006899706B2

(12) United States Patent　　(10) Patent No.: US 6,899,706 B2
Slatkine　　(45) Date of Patent: May 31, 2005

(54) ISOTOPIC LASER FOR THE ORAL CAVITY AND USE OF THE SAME

(75) Inventor: Michael Slatkine, Herzlia (IL)

(73) Assignee: Inolase 2002 Ltd. (IL)

( * ) Notice: Subject to any disclaimer, the term of this patent is extended or adjusted under 35 U.S.C. 154(b) by 0 days.

(21) Appl. No.: 10/337,837

(22) Filed: Jan. 7, 2003

(65) Prior Publication Data

US 2003/0158544 A1 Aug. 21, 2003

Related U.S. Application Data

(60) Provisional application No. 60/347,092, filed on Jan. 9, 2002.

(51) Int. Cl.[7] .............................................. A61B 18/22
(52) U.S. Cl. ............................ 606/3; 128/898; 606/13; 606/19
(58) Field of Search ....................... 128/898; 606/3–10, 606/15–16

(56) References Cited

U.S. PATENT DOCUMENTS

| 4,736,743 A | | 4/1988 | Daikuzono | |
| 5,062,842 A | | 11/1991 | Tiffany | |
| 5,125,925 A | * | 6/1992 | Lundahl | 606/15 |
| 6,122,300 A | * | 9/2000 | Freiberg et al. | 372/25 |

OTHER PUBLICATIONS

Data sheet from LTG Laser Group, Inc, sealed CO2 Lasers, from wed page dated Nov. 2001.*
Israel, M., "Use of the CO2 Laser in Soft Tissue and Periodontal Surgery," Practical Periodontics & Aesthetic Dentistry, vol. 6, No. 6, pp 57–64.
Barak, S., Mintz, S., Katz, J., "The Role of Lasers in Ambulatory Oral Maxillofacial Surgery," Operative Techniques in Otolaryngology—Head and Neck Surgery, vol. 5, No. 4, 1994, pp. 244–249.
Walsh, L., "The Use of Lasers in Implantology: An Overview," Journal of Oral Implantology, vol. XVIII (4), 1992, pp. 335–340.
Wigdor, H., Walsh Jr., J., Mostoff, R., "The Effect of the CO2 laser(9.6 micrometer) on the Dental Pulp in Humans," Lasers in Dentistry VI, Proceedings of SPIE, vol. 3910, San Jose 2000, pp. 158–163.
Coluzzi, D., "An Overview of Laser Wavelengths Used in Dentistry," Dental Clinics of North America, vol. 44, No. 4, Oct. 2000, pp. 753–765.
Irvine, W., Pollack, J., "Infrared Optical Properties of Water and Ice Spheres,"Icarus, vol. 8, No. 2., Mar. 1968, pp. 324–360.
Remacle, M., Lawson, G., Watelet, J., "Carbon Dioxide Laser Microsurgery of Benign Vocal Fold Lesions: Indications, Techniques, and Results in 251 Patients," Ann. Otol. Rhinol. Laryngol., 108(2), Feb. 1999, pp. 156–164.
Grossenbacher, R., "CO2 Laser Surgery for Benign Lesions of the Vocal Cords," Adv. Otholaryngology, vol. 49, 1995, pp. 158–161.

* cited by examiner

*Primary Examiner*—Roy D Gibson
*Assistant Examiner*—Henry M Johnson, III
(74) *Attorney, Agent, or Firm*—Lerner, David, Littenberg, Krumholz & Mentlik, LLP

(57) ABSTRACT

Method and apparatus for effecting a bloodless incision of soft tissue within the oral cavity. A standard laser is converted into an isotopic laser replacing the gas in the discharge tube of the standard laser with isotopic gas without replacing other constituents of the gas of the standard laser. The thickness of anti-reflection coating on the windows of the discharge tube is increased and the reflectivity of the reflectors is increased to a maximal value. The pulse duration of the laser is decreased and the converted laser directing to a desired target location of soft tissue within the oral cavity. The target location is at a penetration depth deep enough to avoid bleeding and distant enough from the soft tissue to minimize collateral damage. The converted laser fired to the target location at a wavelength and at an energy level suitable to effect the bloodless incision.

18 Claims, 10 Drawing Sheets

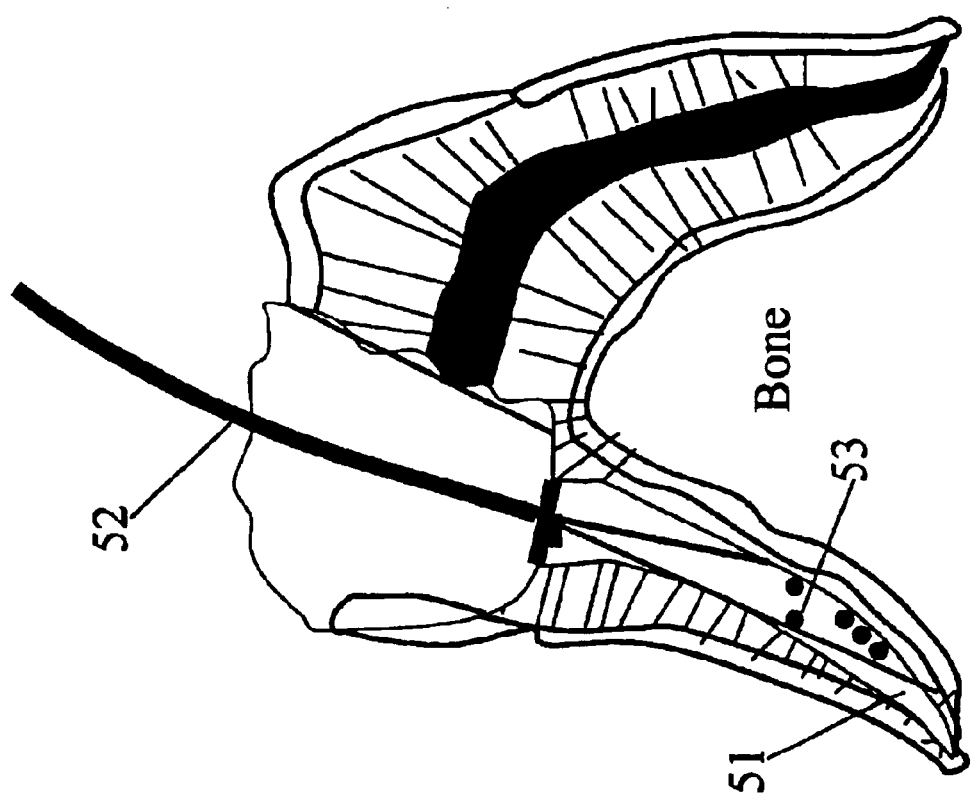

ISOTOPIC LASER FOR THE ORAL CAVITY AND USE OF THE SAME

This application claims the benefit of the filing date of U.S. Provisional Patent Application No. 60/347,092 filed Jan. 9, 2002, the disclosure of which is hereby incorporated herein by reference.

FIELD OF THE INVENTION

The invention relates to surgical lasers used in dentistry, oral surgery and in the throat, and particularly to an isotopic 13C16O2 laser used for treatment in the oral cavity.

BACKGROUND OF THE INVENTION

Diode lasers as well as Carbon dioxide (12C16O2) lasers are used as incision and ablation surgical tools to treat soft tissue in dentistry as well as in oral maxillofacial surgery. The reasons that lasers are used for soft tissue incisions include a lack of bleeding, high cutting precision and minimal collateral damage. The surgical site is also automatically sterilized and post operative edema is considerably reduced, while healing is faster, as compared to non-laser surgery.

Precise incision with diode lasers is described in U.S. Pat. No. 4,736,743. The Carbon Dioxide lasers broadly utilized in dentistry and oral surgery emit radiation at a wavelength of 10.6 microns. The radiation emitted by the lasers penetrates 30–50 microns deep into tissue, depending on the water content of the tissue. The laser beam is usually focused on the tissue with a focusing lens, often made of ZnSe, which generates a spot size of 80–150 microns. The laser provided hemostatic incisions at power levels ranging from approximately 5–20 W for a continuous working laser, at variable speeds. The laser can also be operated in a superpulse mode such as produced by Sharplan with a train of individual pulses of approximately 100–300 microseconds duration and a peak power ranging from approximately 300 to 1000 W and repetition rates of approximately 50–300 pps. When operated in a superpulse mode, the thermal damage created by the thermal diffusion of absorbed heat is minimized and is close to 50–100 microns. Since the thermal relaxation time of tissue at 50 microns depth is approximately 200 microseconds, further reduction of pulse duration does not substantially further reduce collateral damage. Another pulse mode utilized with $CO_2$ lasers is the ultra pulse produced by Coherent USA. The energy content of ultrapulses is usually close to 50–500 millijoules/pulse.

The applications of a $CO_2$ laser in oral surgery include gum treatment (e.g. gingivectomy and other periodontal procedures), implant exposure in second stage implantology (excluding first stage implantology) and many other oral treatments. The procedures are very common. [See for example "Use of the $CO_2$ Laser in Soft Tissue Periodontal Surgery," M. Israel, Practical Periodontics & Aesthetic Dentistry, Vol. 6, No. 6, pp. 57; "The Role of Lasers in Ambulatory Oral Maxillofacial Surgery," Barak et al, Operative Techniques in Otolaryngology—Head and Neck Surgery, Vol. 5, No. 4, 1994; and "The Use of Lasers in Implantology: An overview," Walsh, Journal of Oral Implantology, Vol. XVIII (4), 1992.]

When using a conventional 12C16O2 laser, surgeons are aware of the necessity to be very careful not to penetrate too deep into gum tissue in order to avoid any damage to the underneath bone or of the tooth hard tissue. That is one of the reasons that lasers, e.g. 12C16O2 lasers, are not used to expose bones in the first implantology stage since heat, which may diffuse from the incision made with a 12C16O2 laser, may damage the bone. Another reason is that the tissue loss due to evaporation as well as collateral damage is too large and suture of tissue at the end of the procedure is not practically feasible. A $CO_2$ laser with a wavelength of 10.6 microns is not precise enough to perform some major applications such as first stage bone exposure, although it is suitable for various other applications. Yet, as already mentioned, its residual thermal damage, which is usually greater than 150–200 microns, renders this laser risky if not used with extreme care.

Although the 10.6 microns $CO_2$ laser has been used in the oral cavity by dentists and oral surgeons for over 20 years, the isotopic 13C16O2 carbon dioxide laser which emits radiation at 11.2 microns has never been used in dentistry or in oral maxillofacial surgery. Companies which sell $CO_2$ lasers for dentistry, such as Opusdent, sell 10.6 microns lasers and do not market 13C16O2 isotopic lasers which operate at a 11.2 microns wavelength for dentistry or oral surgery.

In contrast, the utilization in dentistry of an other wavelength emitted from regular 12C16O2 lasers, namely the 9.3–9.6 microns wavelengths range, is discussed in the prior art due to the enhanced absorption of that spectral range in hard tissue such as enamel, dentin or bone. [See "The Effect of the $CO_2$ Laser (9.6 microns) on the Dental Pulp in Humans," H. Wigdor et al, Lasers in Dentistry VI, Proceedings of SPIE, Volume 3910, San Jose 2000.]

A recent review of all the laser wavelengths used in dentistry appears in "An Overview of Laser Wavelengths used in Dentistry," Coluzzi D. J, Dent. Clin North Am 2000 October; 44(4):753–65. Isotopic 13C16O2 lasers are not mentioned in that review.

Isotopic 13C 16O2 carbon dioxide lasers are lasers which emit radiation at 11.2 microns. The absorption of radiation at 11.2 microns wavelength is almost twice higher than at 10.6 microns. The absorption coefficient of radiation at 11.2 microns wavelength in water is 1370 $cm^{-1}$, whereas the absorption at 10.6 microns is only 890 $cm^{-1}$ (Irving and Pollack, Icarus, Vol. 8, No. 2, pp. 324–360, March 1968). The penetration depth in tissue is approximately 15 microns. U.S. Pat. No. 5,062,842 by Tiffany describes the use of an isotopic 13C 16 O2 laser in laparoscopic gynecology. The reason for using the isotopic laser in laparoscopy is the creation of a defocusing blooming effect by the normal 12C16O2 insuflation gas which absorbs the laser radiation produced by a normal 12C16O2 laser and the lack of such absorption when an isotopic 13C16O2 laser is used. An isotopic laser has been distributed by Coherent USA for gynecology.

Bone exposure in stage 1 of dental implantology is not performed with 12C16O2 lasers as explained earlier, although there would be a great advantage if that method of exposure were made possible. In bone exposure it is important to incise the soft tissue and the periostum tissue with negligible deterioration of the surrounding tissue or tissue loss so that it would be possible to suture the wound after bone drilling and minimize healing time of the soft tissue. Tissue loss should be minimal. It would be of great advantage to use a laser with the precision of a scalpel (which is currently used), yet with less bleeding. A laser which has a penetration depth in tissue as low as 3 microns is the Erbium laser. However, it is impossible to precisely focus a multimode Erbium laser for precise incisions, and furthermore, bleeding is excessive with an Erbium laser. It would be preferable to use a laser which emits a beam that penetrates deeper in tissue than an Erbium laser beam in order to reduce bleeding, but considerably less than a 10.6 microns laser, which causes too much collateral damage in first stage bone implantology. The laser should also be focused with high precision. Also, since the required laser's penetration depth in tissue is less than with a 12C16O2 laser, it would also be possible to efficiently utilize superpulses with a shorter duration than currently used with 12C16O2 lasers in dentistry.

The use of such a laser would also considerably enhance the safety of procedures, including most gingival procedures, performed very close to hard tissue or ligaments surrounding the teeth, which should not be heated. Also exposure in second stage implantology would be improved.

An other dental procedure which has been described in the prior art is root canal sterilization with the aid of a laser. A laser beam delivered through a thin fiber is aimed at the root canal, resulting in the destruction of bacteria while making visits to the dentist for antibiotic sterilization unnecessary prior to filling. Nd:YAG lasers, as well as regular 12C16O2 lasers, have been used for that procedure. Also, Erbium lasers with a 3-micron penetration depth have been used. The 13C16O2 isotopic laser has never been described for that procedure. The reduction of the penetration depth by 50% as compared to 12C16O2 lasers considerably increases the bacteria temperature by a factor of 2 (bacteria are 1–10 microns large), resulting in a higher destruction efficacy, or in a reduction of the necessary power to perform sterilization.

The smaller penetration depth of a laser as described hereinabove has an additional advantage in few lingual procedures, such as the treatment of leukoplacia which is treated by superficial removal of lingual tissue with a scanner for example.

A procedure performed in aesthetic dentistry is gum resurfacing and gum depigmentation. The procedure currently necessitates an Erbium laser since it provides superficial ablation and only pigmented tissue should be removed without creating a scar. Very often, a dentist who owns a 12C16O2 laser will not purchase another laser specifically for gum resurfacing. The use of a 15-micron penetrating isotopic laser will provide both bloodless incisions with underlying safety to hard tissue and gum resurfacing capabilities.

Another oral application which requires a smaller absorption depth than that attained with regular 12C16O2 lasers is the treatment of taste buds and oral pockets which are the cause of bad breath (halitosis), such as on the surface of the tonsils.

It is clear from that there is a need for a laser with an absorption depth of approximately 15 microns in soft tissue for the applications of dentistry and oral maxillofacial surgery.

Hard tissue has been treated in the past with a conventional 12C16O2 laser without reasonable success. The main problem was the treatment of enamel. Treatment of dentin gave better results, although 9.6 microns is considered the preferred wavelength with 12C16O2 lasers for hard tissue. 13C16O2 lasers operating in the 11.2 microns band have never been used on hard tissue.

Fiber delivery systems are currently being used with the regular 12C16O2 lasers in a variety of medical applications, including oral applications. 13C16O2 lasers have been used in gynecology due to the insuflation problem mentioned earlier. The 13C16O2 lasers operating in the 11.2-micron band are used with a surgical laparoscope and focusing optics. The combination of an isotopic 13C16O2 lasers and fiber delivery systems have not been identified as useful in prior art.

12C16O2 lasers operated in the superpulse mode are extensively used in the treatments of vocal cords which require extreme precision. Comprehensive descriptions of the use of state of the art lasers in the treatment of vocal cords are presented in "Carbon Dioxide Lasermicrosurgery of Bening Vocal Fold Lesions: Indications, Techniques and Results in 251 patients," Remacle M et al, Ann Otol Rhinol Laryngol, February 1999, 108(2): 156–64 and in "$CO_2$ Laser Surgery on Bening Lesions of the Vocal Cords," Grossenbacher R, Adv Otholaryngology, 1995, 49: 158–61. The use of an isotopic 13C16O2 laser with only 15 microns penetration depth and possible shorter pulse duration associated with shorter tissue relaxation time for shorter penetration depth and smaller collateral damage has not been identified in the prior art.

An object of the invention is to provide dentists and oral maxillofacial surgeons with an incision tool to be used in the oral cavity, which enables a quick, bloodless and precise incision of soft tissue in the vicinity of hard tissue, without causing excessive damage to adjacent or underlying tissue, and without causing excessive tissue loss.

An object of the invention is to provide a laser for use in the oral cavity which emits radiation which penetrates approximately 15 microns in soft tissue.

An additional object of the invention is to considerably enhance the precision of laser surgery in dentistry and oral maxillofacial surgery, when compared to the precision attained by conventional 12C16O2 lasers operated at 10.6 microns.

An additional object is to provide dentists and oral maxillofacial surgeons with a laser which can efficiently perform Stage 1 bone exposure in dental implantology by laser incision of soft tissue and the periostum with good tissue preservation and minimal tissue loss, without significant bleeding and damage to the underlying bone.

An additional object is to provide dentists and oral maxillofacial surgeons a laser which allows for incisions of the gingival close to the hard tissue of the teeth or ligaments surrounding the teeth.

An additional object is to provide dentists with a tool which can clear gum pigmentation.

An additional object is to provide oral maxillofacial surgeons with a tool for superficial ablation of tissue on the tongue to treat leukoplakia.

Yet an additional object of the invention is to allow for the treatment of taste buds or pockets which are responsible for bad breath.

Yet an additional object is to provide a laser which is considerably more effective for the sterilization of a root canal than a 12C16O2 laser.

Yet an additional object of the present invention is to treat vocal cords with a higher precision than attainable with a 12C16O2 laser.

SUMMARY OF THE INVENTION

The present invention is directed to a method for effecting a bloodless incision of soft tissue within the oral cavity, comprising:
  a) Converting a standard laser into an isotopic laser by-
    i. replacing the gas in the discharge tube of said standard laser with isotopic gas without replacing other constituents of the gas of said standard laser;

ii. increasing the thickness of anti-reflection coating on the windows of the discharge tube;

iii. increasing the reflectivity of the reflectors to a maximal value;

iv. decreasing the pulse duration of the laser;

b) Directing said converted laser to a desired target location of soft tissue within the oral cavity, said target location being at a penetration depth deep enough to avoid bleeding and distant enough from said soft tissue to minimize collateral damage;

c) Firing said converted laser to said target location at a wavelength and at an energy level suitable to effect said bloodless incision.

The precision of the incision is preferably similar to that of an incision made by a scalpel.

The target location is selected from the group of periostum, external layer of dentin, mucosa to expose a bone in first stage implantology, root canal for root canal sterilization, pockets between the gums and the teeth, tongue tissue, tonsil tissue and gum tissue.

In one aspect, the penetration depth is approximately 15 microns within soft tissue.

In one aspect, the pulse duration of the laser ranges from approximately 25 to 50 microseconds in a superpulse mode.

In another aspect, the wavelength of a laser beam is approximately 11.2 microns.

In another aspect, the pulse duration is reduced by using a continuous working laser and scanning the target location. The target location is preferably scanned at such a rate that the dwelling time of a laser beam on the soft tissue is less than 100 microseconds.

The present invention is also directed to a method for the treatment of vocal cords, comprising:

a) Converting a standard laser into an isotopic laser byi. replacing the gas in the discharge tube of said standard laser with isotopic gas without replacing other constituents of the gas of said standard laser;

ii. increasing the thickness of anti-reflection coating on the windows of the discharge tube;

iii. increasing the reflectivity of the reflectors to a maximal value;

iv. decreasing the pulse duration of the laser;

b) Directing said converted laser to a nodule on the vocal cord;

c) Firing said converted laser to said nodule at a wavelength and at an energy level suitable to vaporize said nodule without causing thermal damage to a vocal fold.

The pulse duration is less than 50 microseconds.

The present invention is also directed to apparatus suitable for treatment within the oral cavity, comprising an isotopic 13C16O2 laser operated at approximately 11.2 microns, a beam delivery system and means for directing a laser beam to a target location within the oral cavity.

The laser is a pulsed laser or a continuous working laser. The continuous working laser has a power level ranging from 0.5 to 60 W. The pulsed laser has a power level ranging from 3 to 30 W. The pulse duration of the pulsed laser is less than 100 microseconds, and preferably less than 40 microseconds. The pulsed laser is operative in a superpulse, ultrapulse or any other pulse mode.

The directing means for a laser beam preferably comprises a fiber or a hollow fiber. The distal end of the directing means may be attached to a focusing lens.

In one aspect, the apparatus further comprises a focusing lens. The focusing lens is adapted to produce a spot size ranging from 30 to 100 microns. The focusing lens may be coated for transmission or reflection of a generated laser beam.

In one aspect, the apparatus further comprises a scanner. The scanner is preferably used, in conjunction with a computer, for the incision of tissue in the form of a line or of a curve. The scanner preferably comprises a pointer placed on tissue within the oral cavity to prevent movement of the scanner during operation. The dwelling time of the scanner on tissue may range from 25 to 200 microseconds, and is preferably less than 100 microseconds.

In one aspect, the apparatus further comprises a surgical microscope and a micromanipulator with a focal length ranging from 300 to 400 mm for use in a surgical procedure conducted in the throat.

The laser is used for dental applications, for oral surgery or for surgical procedures conducted in the throat, such as on the vocal cords.

In one aspect, the laser is used to incise mucosa and periostum tissue, and more particularly, for bone exposure in first stage dental implantology.

In one aspect, the laser is used to perform any of the following procedures: gum incisions, gum tissue ablations, gum tissue depigmentation, tongue tissue ablations or incisions, tonsil incisions or ablations, treatment of bad breath, disinfection of a root canal, disinfection of pockets between the gums and the teeth, incision of the lips, ablation of tissue around the lips, treatment of hard tissue, and treatment of vocal cords.

BRIEF DESCRIPTION OF THE DRAWINGS

The above and other characteristics and advantages of the invention will be better understood through the following illustrative and non-limitative detailed description of preferred embodiments thereof, with reference to the appended drawings, wherein:

FIGS. 5a and 5b are schematic drawings of root canal sterilization and gum resurfacing for gum depigmentation effected with an isotopic 11.2 microns 13CO2 laser;

DETAILED DESCRIPTION OF PREFERRED EMBODIMENTS

In accordance with the present invention, an isotopic 13C16O2 laser can be produced by converting a conventional commercial 12C16O2 laser, which is currently used in dentistry, oral maxillofacial surgery or ENT surgery (Ear, Nose and Throat), such as the 15F, 20C, 30C or 40 C DC excited lasers produced by LUMENIS, into a 13C16O2 laser. A 12C16O2 laser can be converted in the following way: a) replacing the standard 12C16O2 gas utilized in the discharge tube with standard commercial isotopic 13C16O2 gas, while the other components of the gas mixture, including $N_2$ and Xe, can essentially be preserved; b) modifying the anti-reflection coating on the tube windows from 10.6 microns to 11.2 microns; c) modifying the reflectors to a maximal reflectivity of 11.2 microns; and d) modifying the pulse duration of the laser in the case of a superpulse mode to a shorter pulse duration of 25–50 microseconds. Another approach is to convert RF excited lasers to 11.2 microns. In that case it is often easier to attain a shorter pulse duration due to the faster rise time of the laser plasma.

Another method of attaining short dwelling time duration on tissue is to use a continuous working laser with a fast scanner. The scanner may be a galvanometric scanner or a scanner which utilizes DC motors. By scanning at a fast rate so that the dwelling time on tissue is 25 microseconds for example, one effectively achieves the equivalent of a 25-microseconds pulse duration, a combination which has never been applied to a 13C16O2 laser in the prior art.

Figure 1:
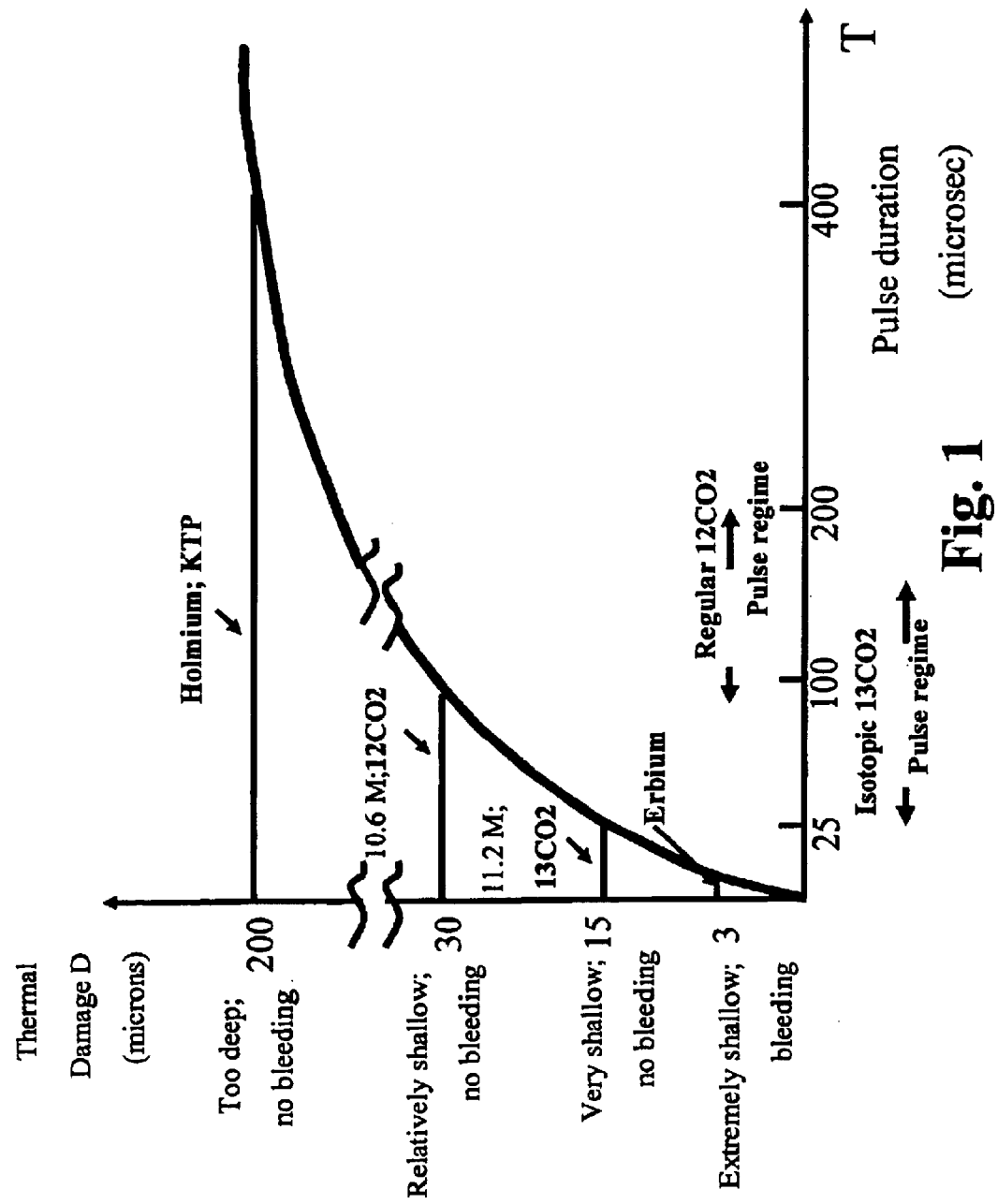
FIG. 1 is a graph of the depth of laser damage as a function of pulse time duration for various wavelengths.

FIG. 1 illustrates the relationship between various wavelengths that are utilized in laser microsurgery and the shortest pulse duration which can be effectively used for minimal tissue damage. The thermal diffusion depth for all wavelengths follows the curve $(27AT)^{1/2}$. However, for each wavelength characterized by a specific penetration depth, the reduction of pulse duration below a threshold T0 will not reduce thermal damage. On the other hand, increase of the pulse duration increases thermal damage. As shown, the pulse duration with a 13C16o2 laser can be advantageously reduced by a factor of 4 as compared to 12C16O2 lasers. The tissue penetration depth of the isotopic laser beam is half the penetration depth of the 12C16O2 laser beam. Since thermal relaxation time is proportional to the square of the penetration depth, the thermal relaxation time of the 13C16O2 laser is 4 time shorter than the relaxation time of the 12C16O2 laser. As a result, the utilization of a 11.2-micron wavelength together with a reduction of pulse duration to 25 microseconds provides microsurgery precision of 15 microns.

Modifications to a 12C16O2 laser which convert it to a 13C16O2 laser reduce the power level by approximately 20%, while the resulting laser power of over 20 W for a former 30 W laser, for example, is high enough for oral and dental applications based on a shallow penetration of radiation in tissue (of approximately a 15-micron penetration depth).

Figure 6:
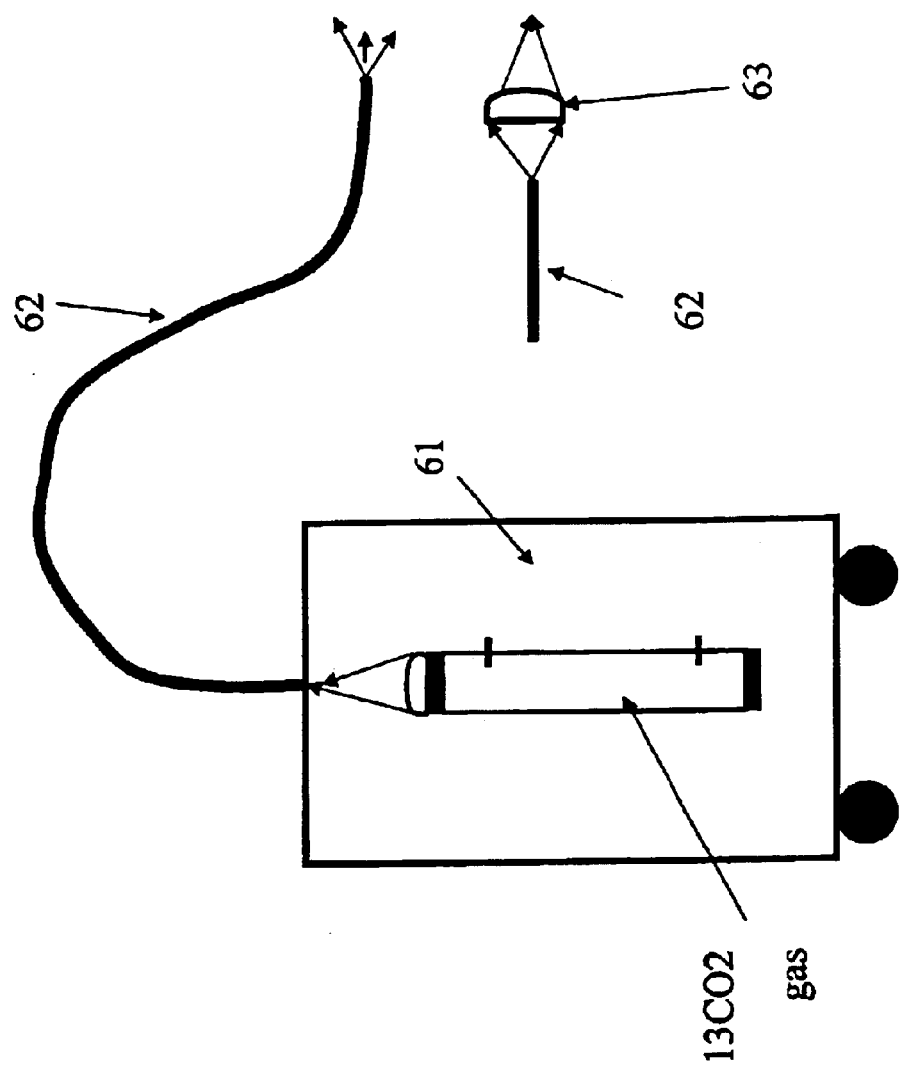
FIG. 6 is a schematic drawing of a fiber delivery system and its use in dentistry, in accordance with the present invention.

FIG. 6 illustrates a fiber 62 which is attached to the isotopic 13C16O2 laser 61 for use in the oral cavity. This embodiment can utilize fibers such as produced by Clinicon, USA or LUMENIS. The inside coating can be optimized to 11.2 microns. A lens 63 having a short focal length of approximately 20 microns to 50 mm may be attached at the end of the fiber 62. The lens may be produced from ZnSe, with 11.2 AR coating. A diamond incision tip, such as produced by Clinicon, USA for contact incision, may also be added.

Figure 7:
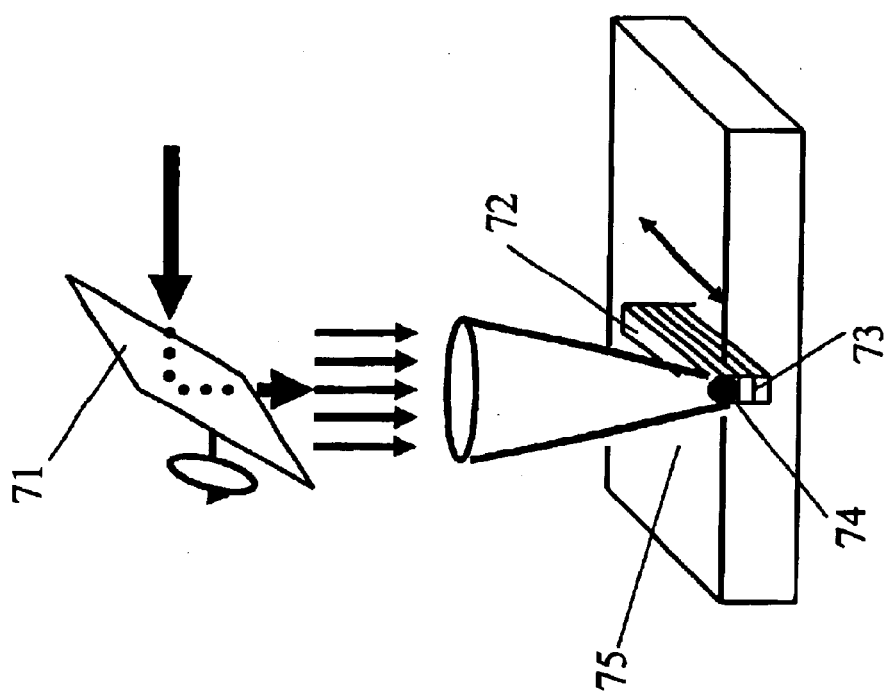
FIG. 7 is a schematic drawing of an incision of soft tissue effected in the mouth or in the throat with an isotopic 13C16O2 laser and a scanner.

The scanner used for incision can be a galvanometric scanner. The surface ablation scanner can be similar to scanners produced by LUXAR or galvanometric scanners produced by SAHAR, USA, LUMENIS, USA or NIDEK, USA. The advantage of using the scanner with a scanning mirror 71 such as in FIG. 7 for producing incision 72 stems from the shallow penetration 73 in tissue 75 and, in some cases, from the necessity to perform a deep incision in tissue. By operating the scanner at a high repetition rate, the scanner will quickly repeat the incision process on the same location without missing the first incision track.

For example, by operating the isotopic 13C16O2 laser with a focal point 74 of 50 microns diameter at a scanning speed of 50 microns/100 microsec (0.5 mm/millisec) and a penetration depth of 15 microns in tissue, a volume of 50 microns×15 microns×5000 microns=37.5×100,000 microns$^3$=37.5/10$^4$ mm cube is removed. The energy required to vaporize a 1 mm cube of tissue is approximately 2.5 joules. An energy level of approximately 120/10$^4$ joules is needed to provide the aforementioned penetration depth, or a laser of power level 120*10$^{-4}$ joules/10$^{-2}$ seconds= 1.2 W. Therefore an isotopic 13C16O2 laser with a power level of a few Watts will provide a 5-mm incision with a dwelling time of 100 microseconds on each spot having a 50-microns size. For each 1-mm deep incision, approximately 80 layers, in which each layer has a 15-micron depth, need to be removed. Thus, if each layer is removed within 10 milliseconds, a scanner is operated only for a duration of 0.8 seconds. It would be difficult to attain such a precision without a scanner since the hand of a surgeon makes a motion within a period of 0.8 seconds.

The use of galvanometric or other scanners practically enables scanning 5 mm within 10 milliseconds. These scanners are capable of scanning a surface area which consists of over 50 lines within 100 milliseconds. As a result, an incision line may be scanned with a 25 microseconds dwelling time.

Quick and precise incisions may be achieved by use of a cylindrical lens which focuses the beam on the tissue and generates a narrow slit shape.

Figure 4A:
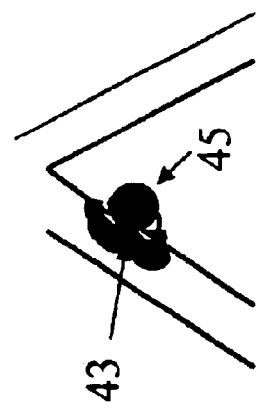
FIG. 4a is a schematic drawing illustrating a nodule on a vocal cord before treatment.
Figure 4B:
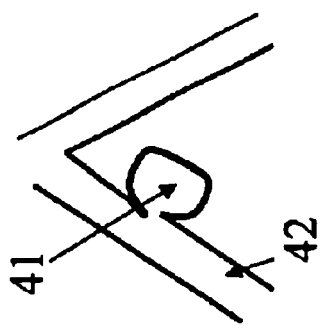
FIG. 4b is a schematic drawing illustrating the effect of treatment with a standard 12CO2 laser.
Figure 4C:
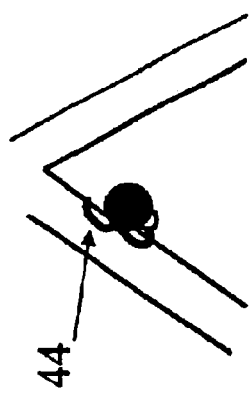
FIG. 4c is a schematic drawing illustrating the effect of treatment of vocal cords with an isotopic pulsed 13C16O2 laser.

The micromanipulator used for ENT microscopes with a focal length of 300–400 mm for the treatment of vocal cords can be similar to the micromanipulators produced by LUMENIS, with a modification of a coating of 11.2 microns wavelength. The advantage of using a 11.2 micron wavelength beam on the vocal cords is depicted in FIG. 4*a*, wherein a nodule 41 formed on the vocal cord 42 needs be vaporized without creating thermal damage to the thin vocal fold, which would result in scarring and in a voice change. The conventional treatment utilizes a focused standard 10.6 micron 12CO2 laser operated in a superpulse mode at an average power of approximately 3 W (approximately 50-millijoule pulses, 150-microsecond pulse duration at a repetition rate of 60 pulses per second). The size of spot 45 shown in FIG. 4*b* is approximately 150 microns, while the width of the damaged zone 43 is close to 100 microns. The use of 25 microseconds pulses at 11.2 micron wavelength results in a thermal damage zone 44, as shown in FIG. 4*c*, of 15 microns width with a considerably lower risk of vocal fold scarring.

Figure 2:
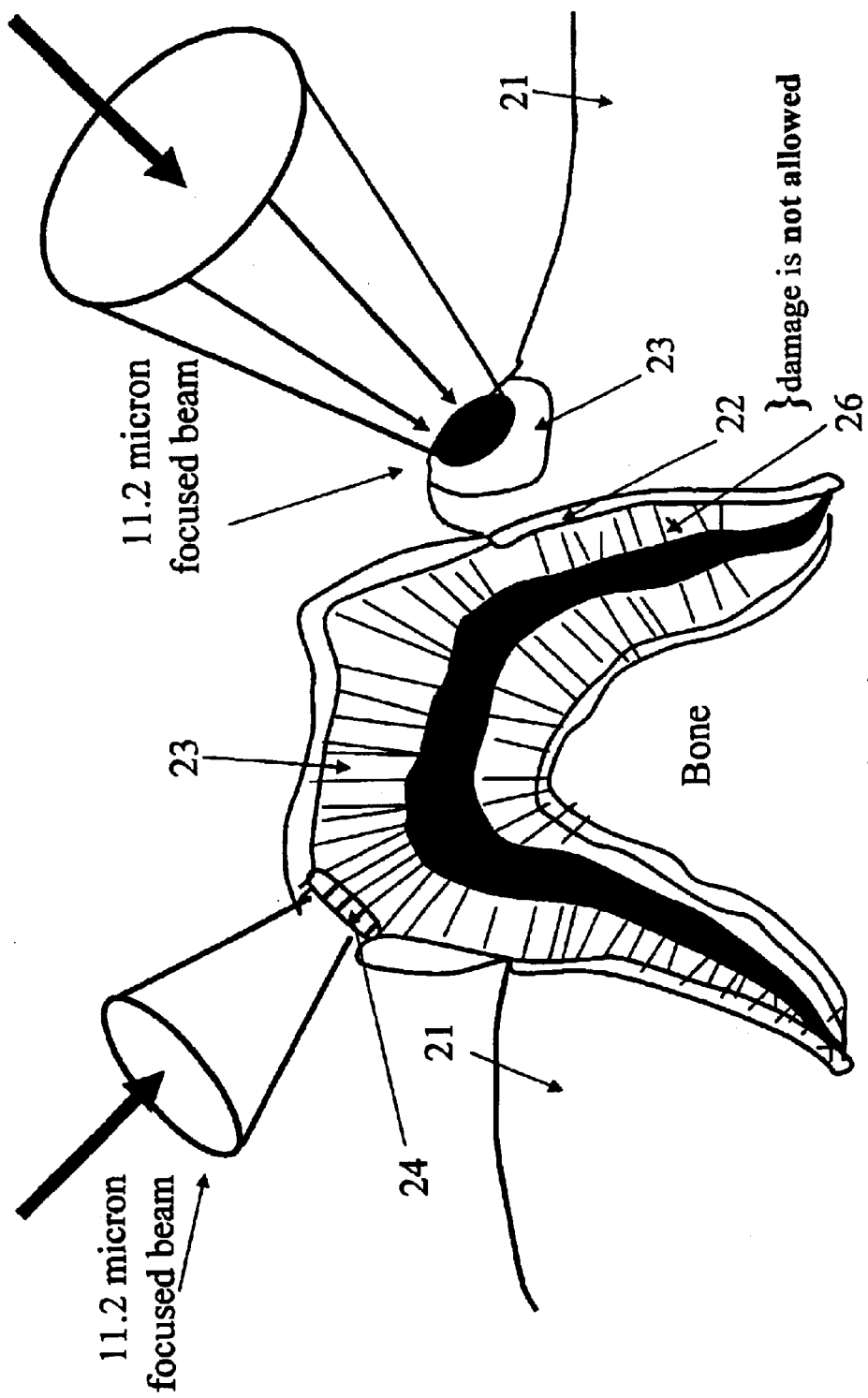
FIG. 2 is a schematic drawing of the treatment of the gums in the vicinity of a ligament and hard tissue with pulsed 11.2 microns wavelength and treatment of the outer layer of dentin tubules with a 13C16O2 laser.

FIG. 2 illustrates the use of a 13C16O2 laser on the gums 21 in the vicinity of the ligament 22 surrounding a tooth (periostum). The very shallow penetration depth of 11.2 microns and minimal collateral damage 23 is safer for the ligament and the hard tissue than the conventional 12C16O2 laser. The treatment of the external layer 24 of the dentin 26 of 11.2 microns is also shown. The tubules 25 are rich with water, thereby enhancing laser absorption at 11.2 microns as compared to 12CO2 and enabling the melting of a thin dentin layer.

Figure 3A:
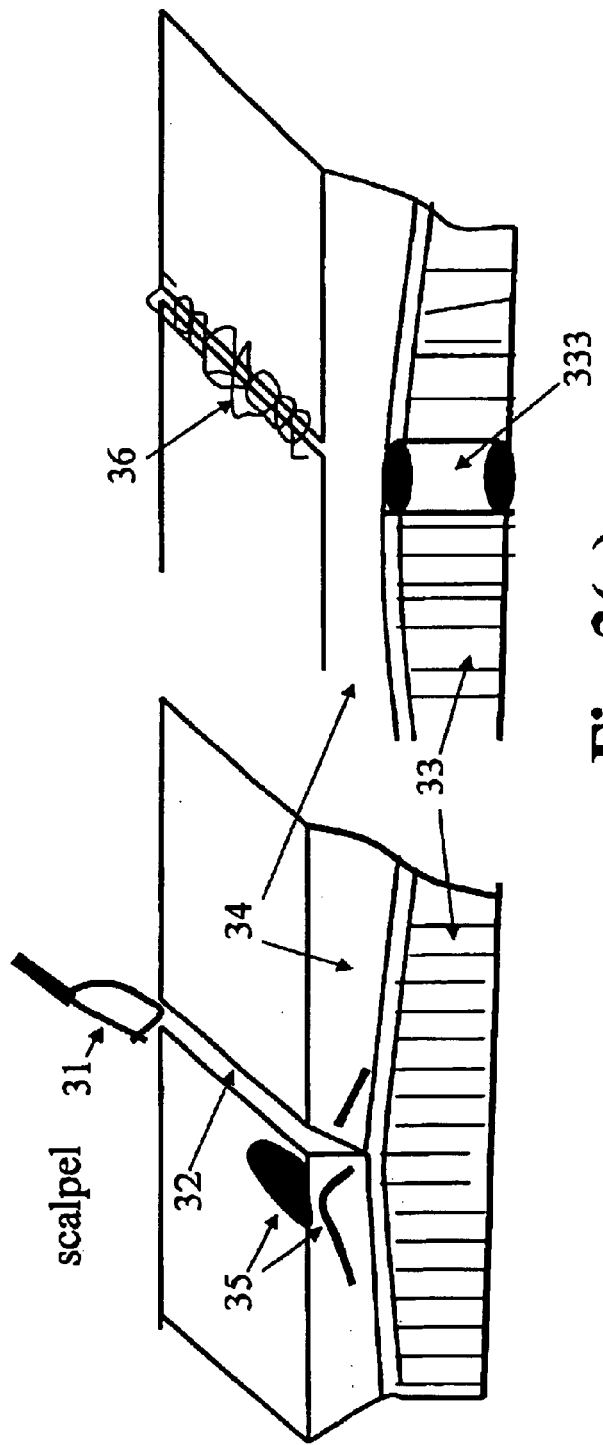
FIG. 3a is a schematic drawing of prior art use of a scalpel in bone exposure in stage 1 implantology.
Figure 3B:
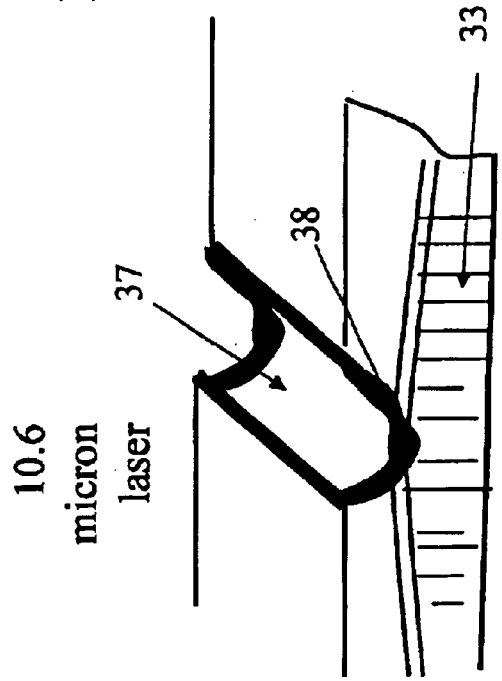
FIG. 3b is a schematic drawing of an incision made with a standard 12C16O2 laser resulting in excessive tissue damage and loss.

FIG. 3 schematically illustrates bone exposure in stage I implantology. By means of scalpel 31 shown in FIG. 3a, a highly precise incision 32 may be achieved in mucosa 34 to expose the bone 33. However, blood vessels 35 are damaged and bleeding occurs. At the end of the procedure suture 36 is performed in order to cover the implant thread 333 without any tissue loss. FIG. 3b illustrates an incision 37 performed with a conventional 12CO2 laser operating at a 10.6-micron wavelength. Although the procedure is free of bleeding, collateral damage 38 is extensive and bone 33 is damaged. Also, tissue loss is extensive and a suture is not possible.

Figure 3C:
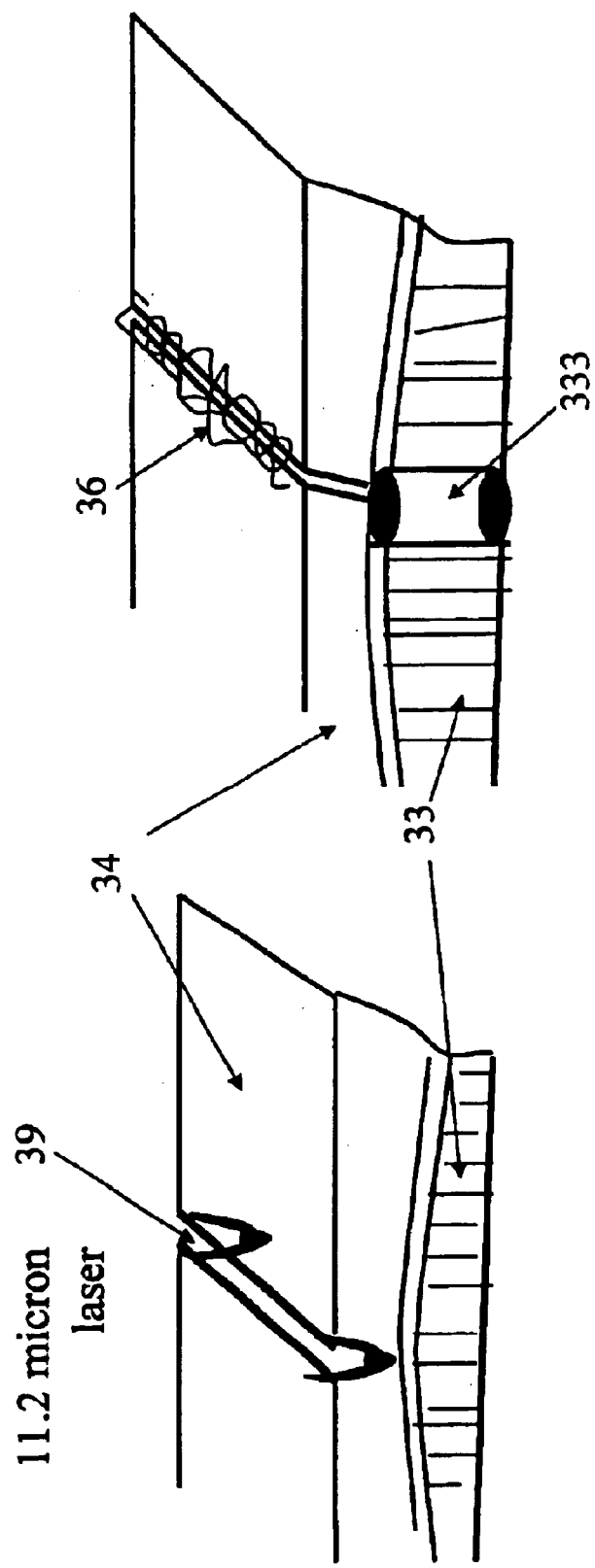
FIG. 3c is a schematic drawing of the use of a pulsed 13CO2 laser according to the present invention resulting in less tissue loss.

In contrast, FIG. 3c illustrates a procedure performed with an isotopic 13CO2 laser operating at a wavelength of 11.2 microns. The procedure is free of bleeding, the incision 39 is narrow without excessive tissue loss, collateral damage is minimal, and a suture is therefore made possible.

FIG. 5a illustrates sterilization of root canal 51 with a 11.2-micron laser and a hollow fiber 52. A power level of 3 W in a CW mode is adequate. The temperature of bacteria 53 following the procedure is expected to be twice the temperature achieved with conventional 12CO2 lasers at the same power level due to the doubled level of absorbed radiation.

Figure 5B:
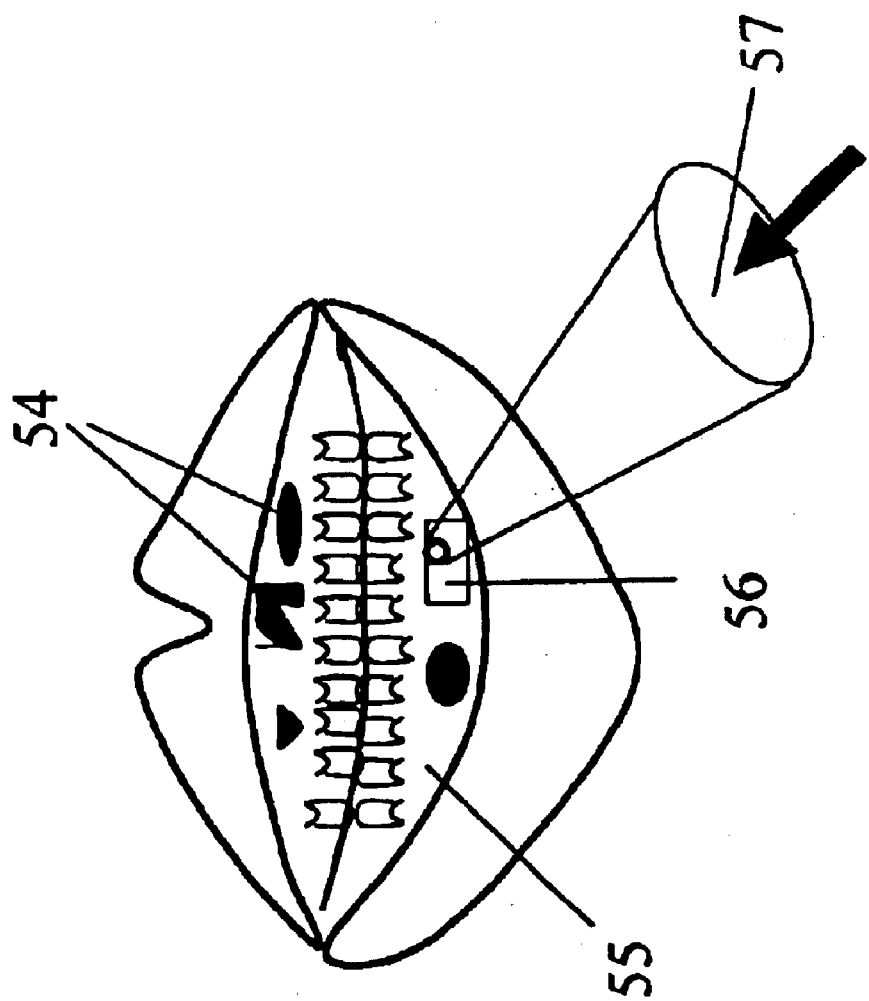

FIG. 5b shows gum depigmentation with the 13C16O2 laser beam 57. Pigmented epithet 54 on gum 55 is ablated at zone 56 with a scanner, for example, at power level of 5 W, spot size of 40 microns and a dwelling time of 25 microseconds. Ablation can also be achieved with the superpulse mode and spot size of 1 mm. Periostum and underlying bone are not damaged.

Figure 8:
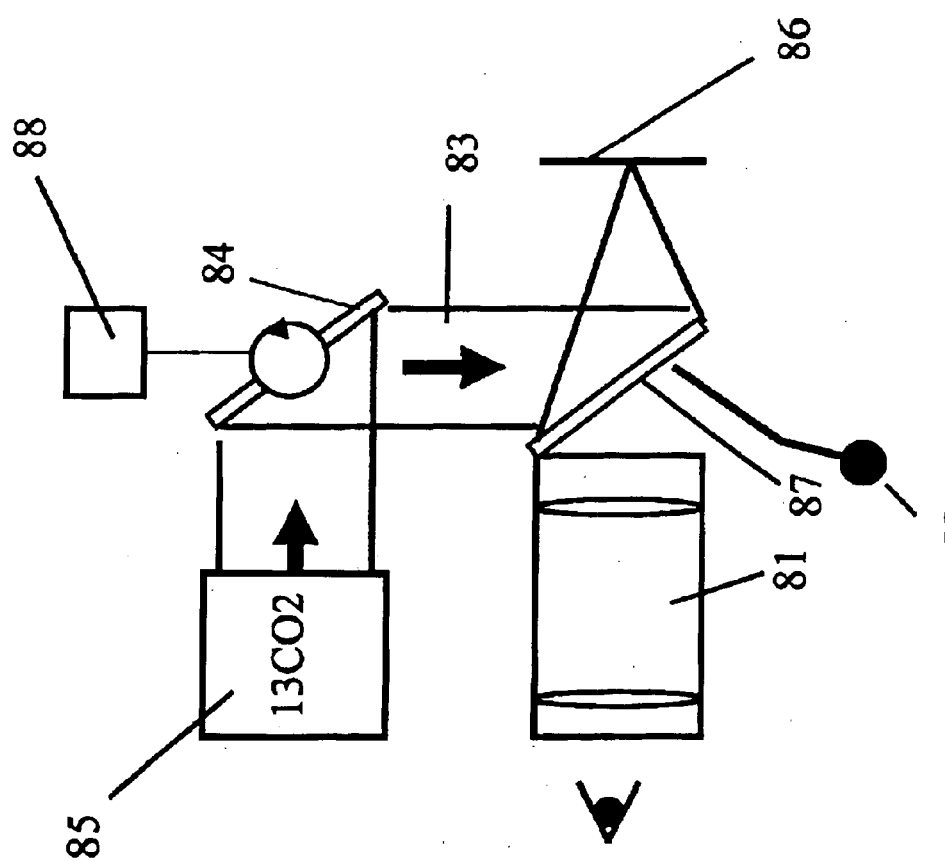
FIG. 8 is a block diagram of an apparatus which comprises a surgical microscope, an isotopic 13CO2 laser, a laryngeal micromanipulator and an attachment to a scanner.

FIG. 8 schematically illustrates a laryngeal surgical microscope 81 such as produced by Zeiss with a micromanipulator 82 having a focal length of 400 mm, such as produced by Lumenis, USA. The dichroic mirror 87 is modified and coated with a coating which provides visibility of the surgical site 86 and over 99% reflectivity at 11.2 microns wavelength. The laser 85 is an isotopic 13CO2, 11.2-micron laser. The laser beam 83 may be reflected from a scanning mirror 84. A scanner 88 is optional.

While some embodiments of the invention have been described by way of illustration, it will be apparent that the invention can be carried into practice with many modifications, variations and adaptations, and with the use of numerous equivalents or alternative solutions that are within the scope of persons skilled in the art, without departing from the spirit of the invention or exceeding the scope of the claims.

What is claimed is:

1. A method for effecting a bloodless incision of soft tissue within the oral cavity, comprising:
   a) providing a laser including a gas-containing discharge tube having a window with an anti-reflection coating;
   b) converting said laser into an isotopic laser by-
      i. replacing a gas in said discharge tube of said laser with an isotopic gas without replacing other constituents of said gas of said laser;
      ii. increasing a thickness of said anti-reflection coating on the window of said discharge tube;
      iii. increasing a reflectivity of a reflector to a maximal value; and
      iv. decreasing a pulse duration of said laser;
   c) directing said converted isotopic laser to a desired target location of a soft tissue within the oral cavity, said target location being at a penetration depth advantageous to avoid bleeding and being sufficiently distant from said soft tissue to minimize collateral damage; and
   d) firing said converted isotopic laser to provide a laser beam at said target location at a wavelength and at an energy level suitable to effect said bloodless incision.

2. The method according to claim 1, wherein precision of said bloodless incision is similar to that of an incision made by a scalpel.

3. The method according to claim 1, wherein said target location is selected from the group consisting of the periostum, external layer of dentin, mucosa to expose a bone in first stage implantology, root canal for root canal sterilization, pockets between the gums and the teeth, tongue tissue, tonsil tissue and gum tissue.

4. The method according to claim 1, wherein said penetration depth is approximately 15 microns within soft tissue.

5. The method according to claim 1, wherein the pulse duration of said laser ranges from approximately 25 to 50 microseconds in a superpulse mode.

6. The method according to claim 1, wherein saidwavelength of said laser beam is approximately 11.2 microns.

7. A method for the treatment of vocal cords, comprising:
   a) providing a laser including a gas-containing discharge tube having a window with an anti-reflection coating;
   b) converting said laser into an isotopic laser by-
      i. replacing a gas in said discharge tube of said laser with an isotopic gas without replacing other constituents of said gas of said laser;
      ii. increasing a thickness of said anti-reflection coating on said window of said discharge tube;
      iii. increasing a reflectivity of a reflector to a maximal value; and
      iv. decreasing a pulse duration of said laser;
   c) directing said isotopic converted laser to a nodule on the vocal cord;
   d) firing said converted isotopic laser to provide a laser beam at said nodule at a wavelength and at an energy level suitable to vaporize said nodule without causing thermal damage to a vocal fold.

8. The method according to claim 7, wherein the pulse duration is less than 50 microseconds.

9. An apparatus suitable for treatment within the oral cavity, comprising an isotopic $^{13}C^{16}O_2$ laser operated at approximately 11.2 microns, a beam delivery system, a surgical microscope, a micromanipulator with a focal length ranging from 300 to 400 mm for use in a surgical procedure conducted in the throat, and means for directing a laser beam to a target location within the oral cavity, wherein the laser is a pulsed laser having a power level ranging from 3 to 15 W and the pulse duration is less than 100 microseconds.

10. A method for making an incision within the oral cavity comprising:
   providing an isotopic $^{13}C^{16}O_2$ laser;
   directing said laser to a desired location of soft tissue within the oral cavity; and
   firing said laser to facilitate the creation of a bloodless incision or ablation.

11. The method according to claim 10, wherein precision of said bloodless incision is similar to that of an incision made by a scalpel.

12. The method according to claim 10, wherein the desired location is selected from the group consisting of a periostum, an external layer of dentin, a mucosa to expose a bone in first stage implantology, a root canal for root canal sterilization, pockets between the gums and the teeth, tongue tissue, tonsil tissue, and gum tissue.

13. The method according to claim 10, wherein a penetration depth of said laser is approximately 15 microns within said soft tissue.

14. The method according to claim 10, wherein a pulse duration of said laser ranges from approximately 25 to 50 microseconds in a superpulse mode.

15. The method according to claim 10, wherein a wavelength of said laser is approximately 11.2 microns.

16. The method according to claim 10, further comprising the step of decreasing a pulse duration of said laser.

17. A method for the treatment of vocal cords comprising:

providing an isotopic $^{13}C^{16}O_2$ laser;

directing said laser to a nodule on the vocal cord; and firing said laser to said nodule at a wavelength and energy level suitable for vaporizing said nodule without causing thermal damage to a vocal fold.

18. The method according to claim 17, wherein a pulse duration of said laser is less than 50 microseconds.

* * * * *